US008892205B2

(12) United States Patent
Miller, III et al.

(10) Patent No.: US 8,892,205 B2
(45) Date of Patent: Nov. 18, 2014

(54) SLEEP APNEA CONTROL DEVICE

(71) Applicant: Otologics, LLC, Boulder, CO (US)

(72) Inventors: Scott Allan Miller, III, Lafayette, CO (US); Jose H. Bedoya, Boulder, CO (US)

(73) Assignee: Otologics, LLC, Boulder, CO (US)

( * ) Notice: Subject to any disclaimer, the term of this patent is extended or adjusted under 35 U.S.C. 154(b) by 0 days.

(21) Appl. No.: 13/707,304

(22) Filed: Dec. 6, 2012

(65) Prior Publication Data
US 2013/0204314 A1 Aug. 8, 2013

Related U.S. Application Data

(60) Provisional application No. 61/567,907, filed on Dec. 7, 2011.

(51) Int. Cl.
*A61N 1/36* (2006.01)
*A61B 5/00* (2006.01)
*A61N 1/378* (2006.01)

(52) U.S. Cl.
CPC ........... *A61N 1/3601* (2013.01); *A61N 1/36178* (2013.01); *A61B 5/4818* (2013.01); *A61N 1/3611* (2013.01); *A61B 5/6867* (2013.01); *A61N 1/3787* (2013.01)
USPC .......................................................... 607/42

(58) Field of Classification Search
None
See application file for complete search history.

(56) References Cited

U.S. PATENT DOCUMENTS

| 4,830,008 | A | 5/1989 | Meer |
| 5,503,146 | A | 4/1996 | Froehlich et al. |
| 2004/0153127 | A1 | 8/2004 | Gordon et al. |
| 2005/0065560 | A1 | 3/2005 | Lee et al. |
| 2008/0194953 | A1 | 8/2008 | Kerber |
| 2010/0094379 | A1 | 4/2010 | Meadows et al. |
| 2010/0241195 | A1* | 9/2010 | Meadows et al. ............. 607/62 |
| 2013/0261693 | A1* | 10/2013 | Gross ........................... 607/42 |

FOREIGN PATENT DOCUMENTS

WO 2008/098365 A1 8/2008

OTHER PUBLICATIONS

International Search Report and Written Opinion for PCT/US2012/068276 dated Feb. 8, 2013.

* cited by examiner

*Primary Examiner* — Michael Kahelin
(74) *Attorney, Agent, or Firm* — Thompson Coburn LLP

(57) ABSTRACT

Disclosed herein are various methods, systems, an apparatuses for determining appropriate situations to treat conditions such as sleep apnea. At appropriate times, treatment can be applied such as through electrical stimulation to a person (e.g., an electrical stimulation of a person's genioglossus muscle in response to detecting that the person is undergoing an obstructive sleep apnea precursor event). In exemplary embodiments, a sensor such as a microphone and/or motion sensor can be used to provide a processor with data to facilitate a determination by the processor as to whether an electrical stimulus should be applied.

55 Claims, 11 Drawing Sheets

Temporal and Spectral Properties of Snoring

Simple vs. OSA Snoring

SLEEP APNEA CONTROL DEVICE

CROSS-REFERENCE AND PRIORITY CLAIM TO RELATED PATENT APPLICATION

This patent application claims priority to provisional U.S. patent application Ser. No. 61/567,907, entitled "Sleep Apnea Control Device", filed Dec. 7, 2011, the entire disclosure of which is incorporated herein by reference.

FIELD

Provided herein as an exemplary embodiment is a fully or partially implantable device that detects and mitigates sleep apnea. In one arrangement, the device electronically detects the signature of snoring and then activates one or more implanted electrodes to increase the tonus of tissue so that it no longer obstructs a patient's airway.

INTRODUCTION

Sleep apnea is a sleep disorder that is present at a rate estimated to be 3% of the general population, with some segments of the population having AHI (Apnea Hypopnea Indices≥5) rates as high as 28%. Sleep apnea presents partial or complete obstruction of the airway during sleep in 99.6% of cases.

The obstruction of the airways is generally due to loss of tonus of the muscles surrounding the upper airways, with subsequent collapse of the tissues, either partially or completely blocking the airways. The tonus is often lost gradually and snoring is often present. See FIG. 1B. Once the patient becomes partially aroused, the tonus of the surrounding musculature increases, pulling the structures out of the airways. See FIG. 1A. This cycle typically repeats itself throughout the night in obstructive sleep apnea. The consequences are hypoxemia and hypoxia followed by partial or full arousal; symptoms include diminished neurocognitive function, increased risk of motor vehicle accidents, hypertension, insulin resistance, and cardiovascular diseases, as well as reduced quality of life. Sleep apnea is also found concomitantly with a variety of health issues.

Several treatments exist for obstructive sleep apnea. These include CPAP (Continuous Positive Airway Pressure), OAT (Oral Appliance Therapy) and surgical revision or reinforcement of the soft tissues. Many patients have a great deal of difficulty with the discomfort and claustrophobia of a CPAP mask, which also restricts sleeping posture. Side effects of OAT include excessive salivation, dry mouth, discomfort of teeth and jaw and temporary changes in the patient's bite, with such complications as jaw pain, permanent occlusal changes and TMJ symptoms. Surgical revision has a failure rate as high as 80% for some procedures, and there are potential complications. Tracheotomy (an opening in the windpipe below the vocal cords) is effective, but there are many of complications. Surgical reinforcement includes the so-called Pillar procedure, which implants polyester rods into the patient's soft palate. Side effects and complications of the pillar procedure include sore throat, changes in voice or sense of taste, foreign body sensation, mucosal edema, infection, allergic reaction to implant material, or implant migration. While the pillar procedure stiffens the soft palate, it can be seen from FIG. 1B that it may not significantly impact sleep apnea in all cases.

Disclosed herein as an exemplary embodiment is an implantable device with an acoustic and/or vibratory sensor (e.g., an accelerometer and/or microphone) that is utilized to alleviate obstructive sleep apnea (OSA) conditions. A sensor output signal from one or both of the sensors is analyzed by the implant for a signature of snoring. Various features are first extracted from the sensor signal(s) which may include spectral content, periodicity, linear predictive filter coefficients, wavelet coefficients, etc. The extracted features are compared to predetermined baseline or threshold values that allow for determining the presence of a snoring event (e.g., typically a precursor to an apnea event is occurring). Such extracted features may be extracted and/or compared utilizing, for example only, a pattern identifier, (such as a hidden Markov model (HMM), neural network (NN), statistical learning system, or the like) to determine whether the patient is or is not snoring. Generally, such extraction identifies a signature of the signal(s) and compares the signature to a known signal (e.g., a snoring signal). When the snoring signature is detected, the device generates an electrical impulse in the muscle mass of the soft tissues adjacent to the throat, increasing their tonus and pulling them and associated structures from obstructing the airway.

While one aspect of the implantable device is directed to treatment of sleep apnea, it has been recognized by the inventors that the implantable device may be utilized for other treatment applications. For instance, the disclosed sleep apnea device, which is in one aspect designed to stimulate the genioglossus muscle may be used in combination with a Vasal Nerve Stimulator (VNS), Further, aspects of the implantable device may be utilized as a muscle stimulator implant with stimulator electrodes implanted in or next to the operative muscles for the process of swallowing (e.g., hyoglossus and/or thyohyoid muscles), to provide periodic muscle contraction for addressing dysphagia. Such an implant may optionally provide sequential stimulation of several muscle groups to provide a sequential swallowing action. This may be performed periodically on a predetermined schedule or on command via a remote control.

A further aspect of the implantable device may be directed to use as a stimulator implant with stimulator electrodes implanted in or next to the salivary glands for treatment of dry mouth (xerostomia or hyposalivation), a disability occurring in stroke, Parkinson's disease, and the like. On command from a remote control and/or periodically under internal control, the stimulator induces the secretion of saliva.

In relation to these latter aspects, there is a noted commonality of the treatments. For instance, the stimulus locations are all within a few inches of each other, all presented in some stroke victims (in some cases simultaneously), and all addressed by the implantable device via electrostimulation. In one arrangement, a single implant device is capable of generating multiple electrostimulation signals with different electrodes at different sites. Such a combined device may have separate operating programs, controls and/or be operated by a single remote control and may be directed to treatment of any or all of OSA, hyposalivation and/or dysphagia individually and/or simultaneously. Further such a combined device may use a single charging system.

In further aspects, the implantable device may provide electro-stimulation for other conditions. Such conditions may require the use of specialized electrodes based on the treated conditions. Such other conditions include, by way of example and not limitations: controlling hypertension by stimulating the carotid sinus barosensory system, and/or using the microphone system to measure and control the systolic and diastolic amplitudes.

In accordance with another exemplary embodiment, disclosed herein is a stimulation system comprising: (1) a sensor configured to generate sensor data, the sensor data including information indicative of whether a condition associated with a sleep apnea-related event exists, the sensor comprising at least one member of the group consisting of a microphone and a motion sensor, (2) a processor configured to (i) process the sensor data to determine whether the condition associated with a sleep apnea-related event is indicated by the sensor data, and (ii) generate a stimulation signal in response to a determination that the condition is indicated, and (3) a stimulation electrode adapted for positioning to provide an electrical stimulation to a sleep apnea treatment location for a person, wherein the stimulation electrode is configured to (1) receive the generated stimulation signal from the processor, and (2) generate an electrical stimulation output in response to the received stimulation signal.

Also disclosed herein as an exemplary embodiment is a stimulation method comprising: (1) processing data to determine whether a condition indicative of a sleep apnea event is indicated by the sound data, the processed data comprising at least one member of the group consisting of sound data indicative of whether a condition associated with a sleep apnea-related event exists and motion data indicative of whether a condition associated with a sleep apnea-related event exists, (2) generating a stimulation signal in response to a determination that the condition exists, and (3) electrically stimulating a sleep apnea treatment location for a person in response to the generated stimulation signal.

Further still, disclosed herein as an exemplary embodiment is a stimulation method comprising: (1) processing data indicative of snoring by a person to determine whether a condition indicative of a sleep apnea-related event exists, (2) generating a stimulation signal in response to a determination that the condition is indicated, and (3) electrically stimulating a sleep apnea treatment location for the person in response to the generated stimulation signal.

In accordance with another exemplary embodiment, the inventors disclose an apparatus comprising a processor configured to operate in a plurality of modes, the modes including a first mode and a second mode, wherein the processor, when in the first mode, is configured to (1) process data comprising information indicative of whether a condition associated with a sleep apnea-related event exists to determine whether the condition exists, and (2) in response to a determination that the condition exists, generate a stimulation signal for indicating that a sleep apnea treatment location for the person is to be electrically stimulated, and wherein the processor, when in the second mode, is configured to generate a stimulation signal for indicating that a sleep apnea treatment location for the person is to be electrically stimulated in accordance with a predetermined schedule.

Moreover, the inventors also disclose as an exemplary embodiment an apparatus comprising a processor configured to (1) operate in a first mode for an initial delay interval, (2) process data comprising information indicative of whether a condition associated with a sleep apnea-related event exists to determine whether the condition exists, (3) after the initial delay interval and in response to a determination that the condition exists, operate in a second mode for a predetermined time period, and (4) after the initial delay interval and in response to a determination that the condition does not exist, operate in a third mode, wherein the processor, when in the third mode, is configured to generate a stimulation signal for indicating that a sleep apnea treatment location for the person is to be electrically stimulated in accordance with a predetermined schedule, wherein the processor, when in the second mode, is configured to generate a stimulation signal for indicating that a sleep apnea treatment location for the person is to be electrically stimulated, and wherein the processor, when in the first mode, is configured to not generate a stimulation signal.

These and other features and advantages of the present invention will be apparent to those having ordinary skill in the art upon review of the following description and drawings.

DETAILED DESCRIPTION

Figures 1A, 1B:
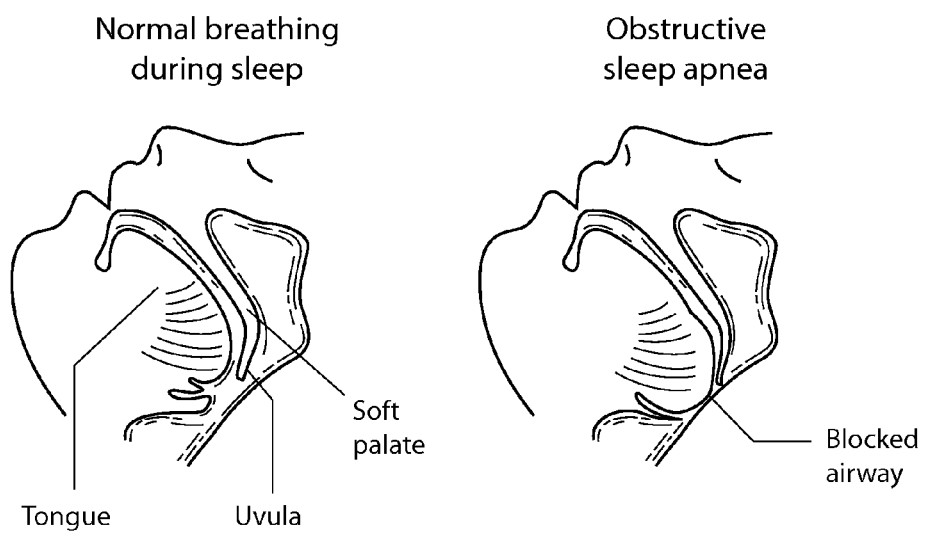
FIG. 1A illustrates muscle tonus in normal breathing during sleep.
FIG. 1B illustrates muscle tonus in Obstructive Sleep Apnea (OSA) sleep.

Reference will now be made to the accompanying drawings, which at least assist in illustrating the various pertinent features of the present invention. The following description is presented for purposes of illustration and description and is not intended to limit the invention to the form disclosed herein. Consequently, variations and modifications commensurate with the following teachings, and skill and knowledge of the relevant art, are within the scope of the present invention. The embodiments described herein are further intended to explain the best modes known of practicing the invention and to enable others skilled in the art to utilize the invention in such, or other embodiments and with various modifications required by the particular application(s) or use(s) of the present invention.

GLOSSARY OF TERMS

Apnea—complete obstruction of the upper airway.

AHI—Apnea and Hypopnea Index. The number of apnea and hypopnea events per hour.

AHIPE—AHI precursors and events. These may be acoustic, vibratory and/or a combination of acoustic and vibratory events. Stated otherwise, features that indicate that apnea or hypopnea are occurring, or are likely to occur soon. Not all snoring qualifies as AHIPE, and AHIPE need not involve snoring. AHIPE is the information about the presence or imminent onset of apnea extracted from acoustic and/or vibrational sensors. It should be understood that there are OSA patients who do not snore in any conventional sense of the word, but from which an AHIPE may still be extracted.

CPAP—Continuous Positive Airway Pressure.

Critical Pressure—(negative) pressure needed to collapse the airway. The larger this value, the harder it is to obstruct the airway.
CSA—Central Sleep Apnea.
Genioglossus—muscle which causes the tongue to pull forward, opening the upper airway.
Glottis—folds of the vocal cords and the space immediately surrounding them.
Hypopnea—reduction in air flow by more than 30%.
Hypoxia—low oxygen level in the bloodstream.
MIC/ACC—microphone and accelerometer assembly.
nCPAP—nasal CPAP
Oropharynx—an opening at the back of the oral cavity between the back of the tongue and the back of the throat.
OSA—Obstructive Sleep Apnea.
Tonus—degree of muscle activation.
UA—upper airway.

Obstructive sleep apnea (OSA) is obstruction of the upper airway by tissue and muscle relaxation (tonus) during sleep. This is in contrast to central sleep apnea (CSA), in which apnea is caused by a problem in the central nervous system. Presented herein is a sleep apnea treatment implant (OSA device) that is intended to address OSA, though it will be appreciated that aspects of the OSA device may have other applications.

As noted above, the superficial mechanism for OSA is straight-forward. The muscle tissue loses tonus (tone) as the subject relaxes into sleep. Initially, this causes a restriction of the airway, resulting in snoring. Further relaxation causes the tissues to collapse into the airway, obstructing it completely. The subject then gradually enters hypoxia until the subject arouses due to discomfort, re-establishing muscle tone and opening the airway. Breathing may stop for 20-40 seconds or longer.

By providing an external positive air pressure, a Continuous Positive Air Pressure (CPAP) can provide enough external pressure to prevent the upper airway from collapsing during sleep. This treatment was found to be an effective approach to addressing OSA in a large meta study. While it is effective, the treatment has several drawbacks, including a face mask and hoses that are buckled to the head during the night, and the variation in optimum pressure with posture. Several variations on CPAP exist that attempt to address its shortcomings. Nasal CPAP (nCPAP) uses a mask which interfaces to the nostrils rather than the entire lower face. However CPAP masks are generally considered are claustrophobia-inducing. This result in patient compliance being relatively poor, with an average of 4 hours or more usage a night considered successful.

Hypoglossal Nerve Stimulation Implants stimulate the appropriate branch of the hypoglossal nerve, which in turn activates the genioglossus, the protrudor muscle of the tongue. This in turn pulls the tissues out of the airway. These devices, while potentially effective, typically require that an electrode cuff surround the hypoglossal nerve. Accordingly, this requires surgical implantation with attendant possibility of damaging the hypoglossal nerve. Such damage has the potential to restrict the ability of a patient to thrust or retract their tongue, adversely affecting their speech, swallowing, and/or breathing. Further, there is a hypoglossal nerve on either side of the jaw line and most hypoglossal stimulation implants stimulate a single hypoglossal and thereby only stimulate muscles on one side body. This results in an asymmetrical and less than complete retraction of the tongue and thereby fails to completely open the upper airway.

An exemplary embodiment for the OSA device as presented herein is distinguished by stimulating the genioglossus muscle directly, rather than a branch of the hypoglossal nerve, and by acting on signals that are precursors to OSA, rather than on signals of respiratory distress. The goal of the OSA device is to significantly reduce the AHI of the patient. The AHI is the number of apnea (complete obstruction of the UA) and hypopnea (defined as reduction of UA flow by 30% or more) events per hour. Further, by implanting a stimulation electrode proximate to the base of the genioglossus muscle near the centerline of the body, muscles on both sides of the body are stimulated improving upper airway opening. Depending upon the desires of a practitioner, the stimulation electrode can be positioned to contact the genioglossus muscle or even be inserted into the mass of the genioglossus muscle to thereby contact an interior portion of the genioglossus muscle.

Figure 2:
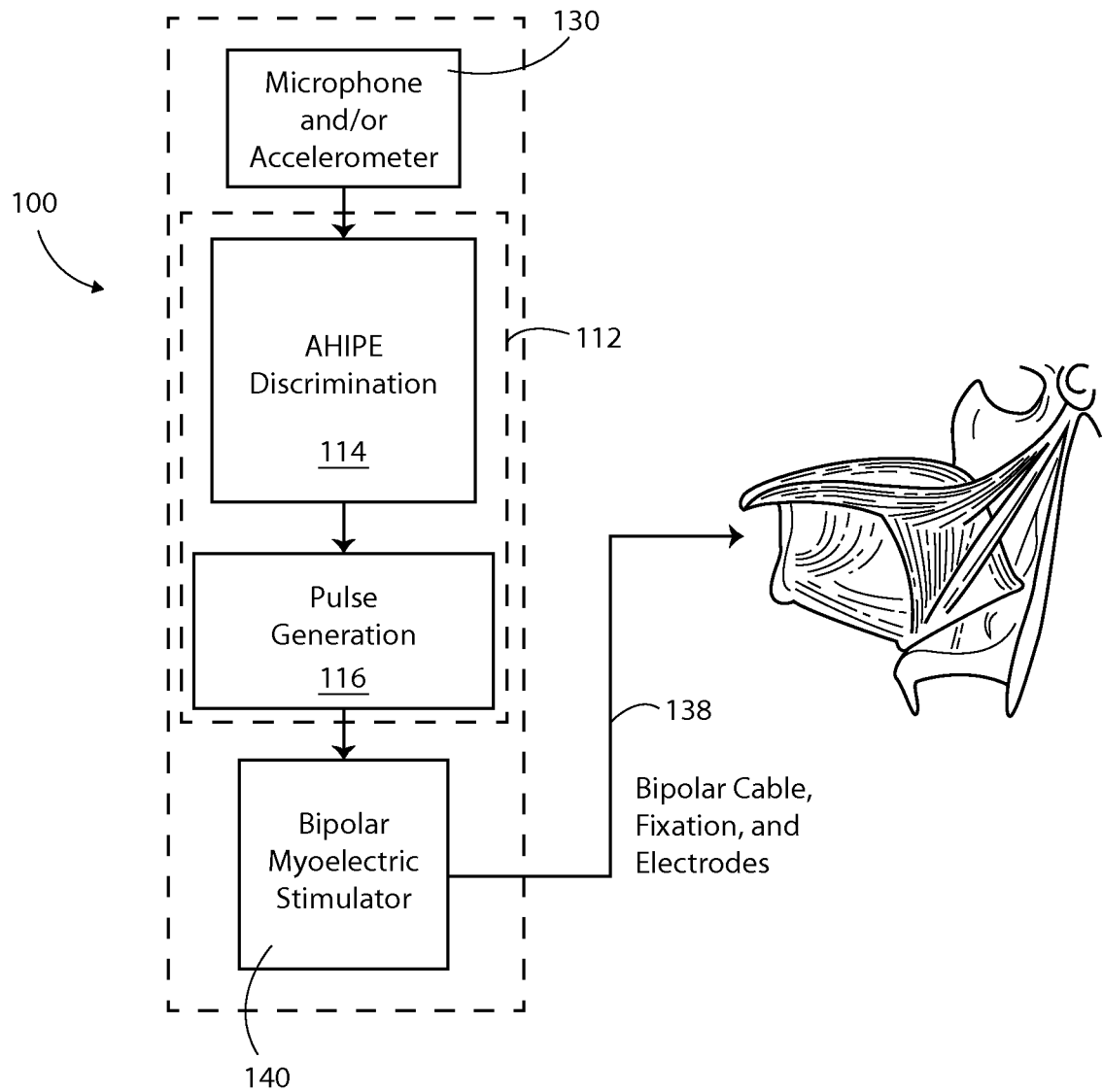
FIG. 2 illustrates a block diagram of an exemplary implantable OSA treatment device.
Figure 3:
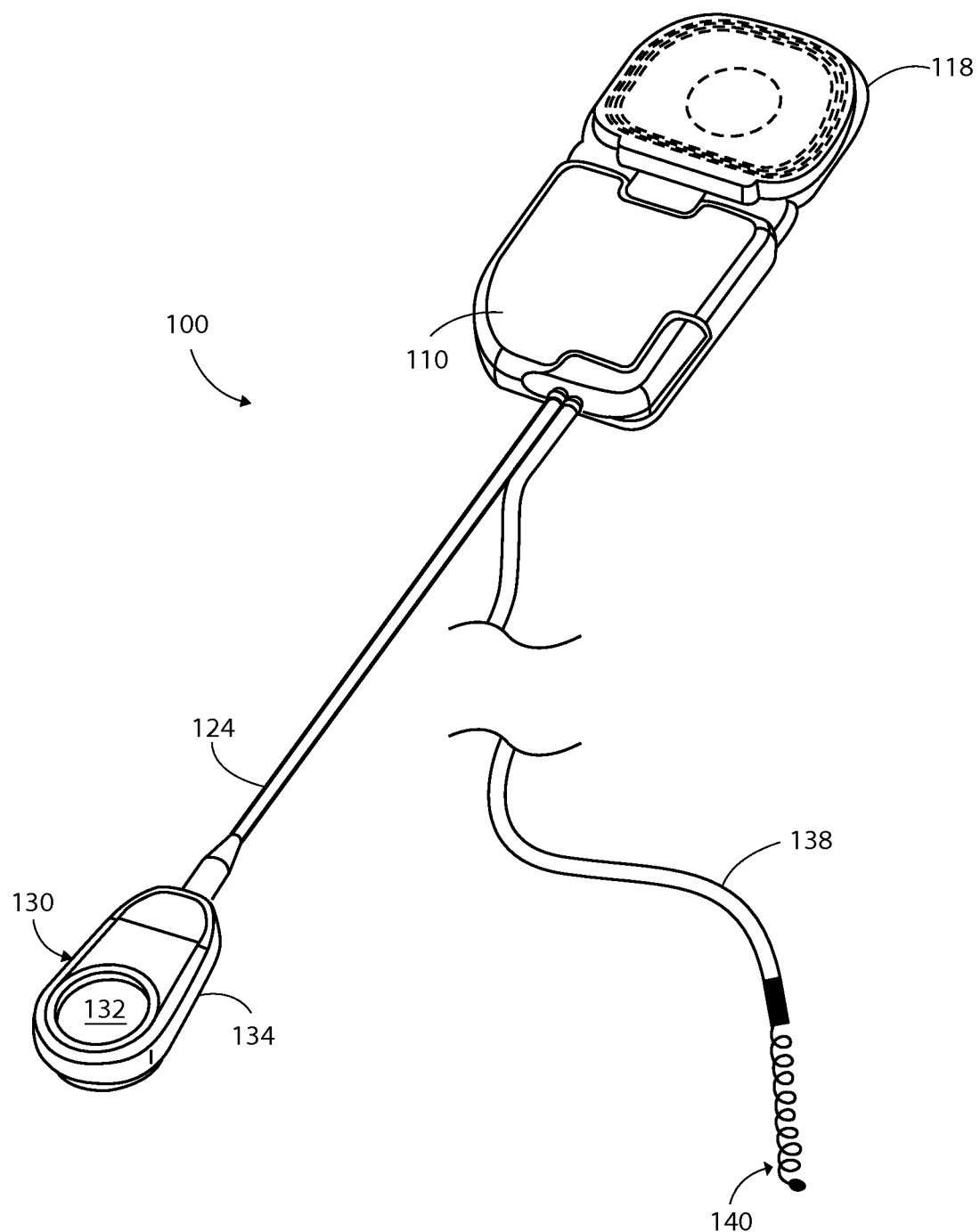
FIG. 3 illustrates an exemplary embodiment of a fully implantable OSA treatment device.
Figure 4:
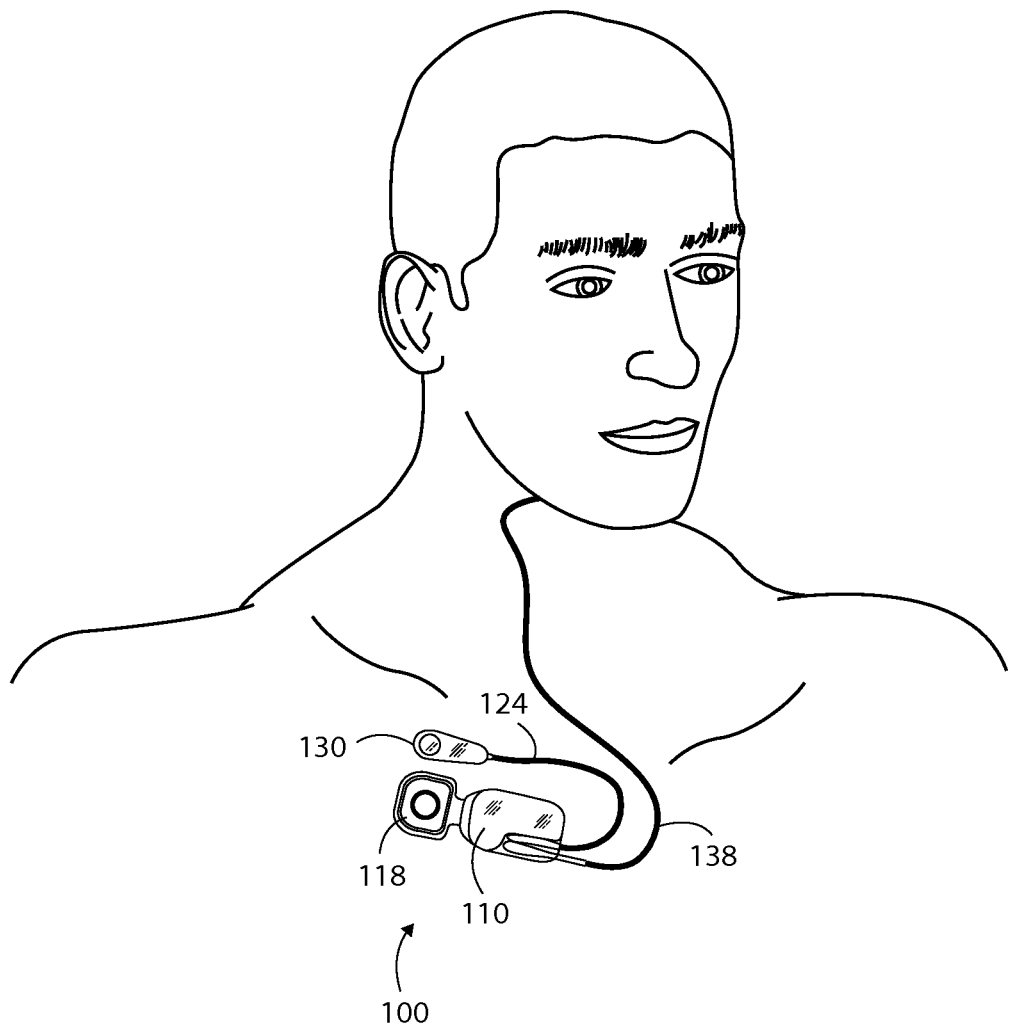
FIG. 4 illustrates the OSA treatment device of FIG. 3 as implanted.
Figure 5:
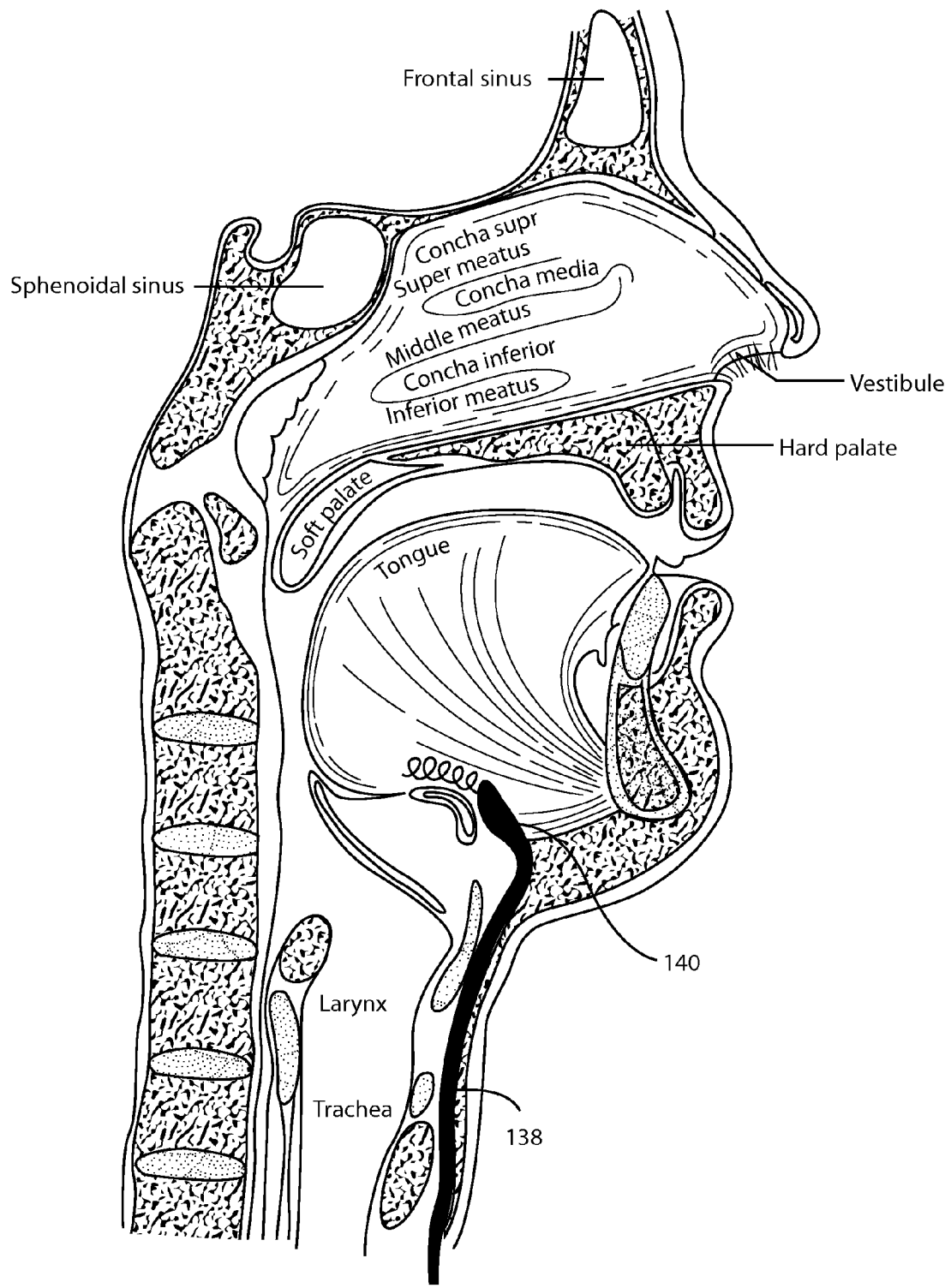
FIG. 5 illustrates a sagittal plane of a portion of a human skull and tissue showing placement of stimulation electrode.

A block diagram of an exemplary OSA device is shown in FIG. 2. It operates by detecting sensory features correlated with AHI precursors and events (AHIPE), and then stimulating the posterior genioglossus to mitigate AHI events. FIGS. 3 and 4 illustrate one embodiment of a fully implantable OSA treatment device 100. As shown, the device include a biocompatible implant housing 110 that may be located subcutaneously at a location below the clavicle of the patient (i.e., sub-clavicularly). The implant housing 110 includes a signal receiver 118 (e.g., comprising a coil element) and is interconnected to a sensor 130 via a signal cable 124. The sensor 130 is configured to sense data indicative of whether a condition associated with a sleep apnea-related exists. An example of a sensor 130 that can be employed includes a microphone, and the many of the examples described herein will discuss the use of a microphone assembly as the sensor 130. However, it should be understood that other sensors can be used in addition to or instead of a microphone, such as a motion or vibratory sensor (e.g., an accelerometer). The implant housing 110 may be utilized to house a number of components of the implantable hearing instrument. For instance, the implant housing 110 may house an energy storage device and a signal processor 112. Various additional processing logic and/or circuitry components may also be included in the implant housing 110 as a matter of design choice. In the present arrangement, the signal processor within the implant housing 110 is electrically interconnected to a stimulation electrode 140. As will be further discussed herein, the stimulation electrode 140 is adapted to provide electrical stimulus to the genioglossus muscle. See FIG. 5.

Figure 11:
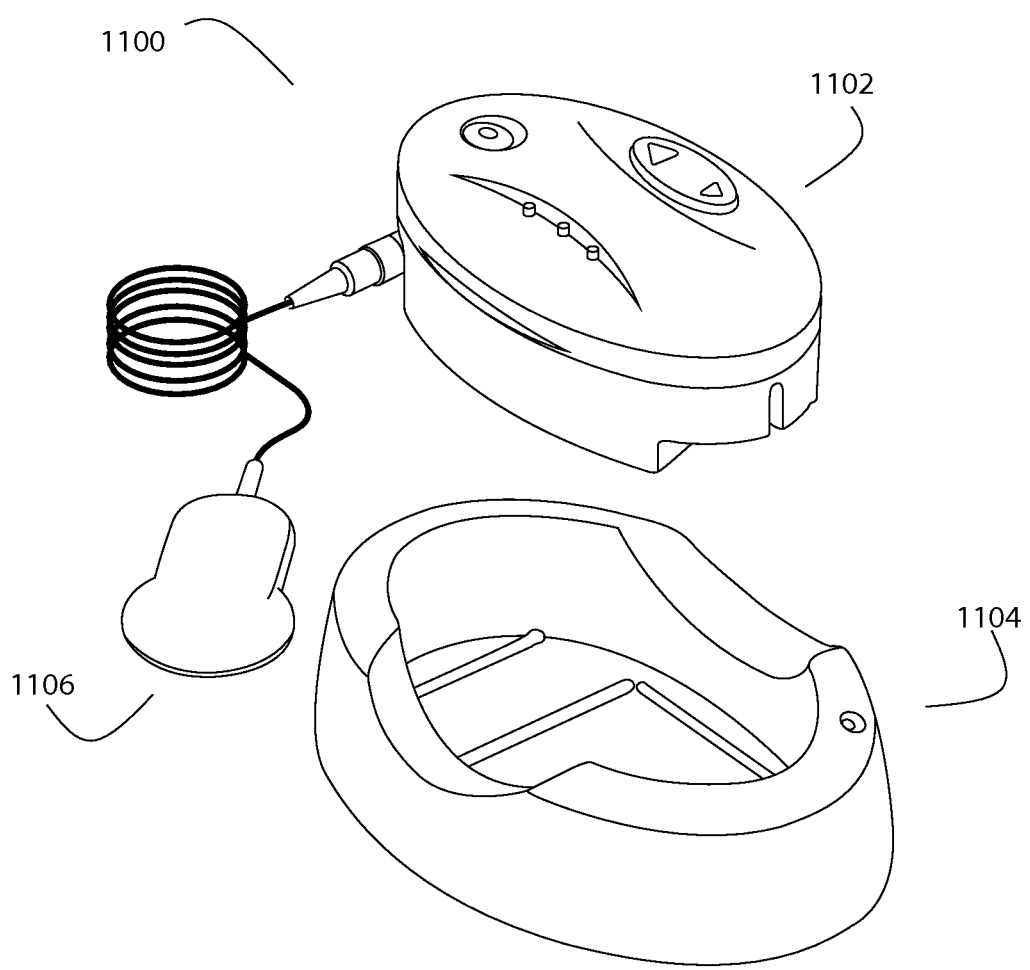
FIG. 11 illustrates an exemplary external charging system.

To power the fully implantable device of FIGS. 2-4, an external charging system 1100 (see FIG. 11) may be utilized to transcutaneously re-charge an energy storage device within the implant housing 110. As shown in the example of FIG. 11, in this regard, the external charging system 1100 may comprise an external charger 1102, a base 1104, and a transmitter 1106. The base 1104 can be configured to provide power to the external charger 1102 from mains power. The external charger 1102 can be configured to provide power for recharging the implantable device as well as provide functionality such as turning the implantable device on/off and/or displaying a status for the implantable device. The transmitter 1106 can be a charger coil or the like that connects with the external charger 1104. The nature of this connection (e.g., via a cord or the like) can render the transmitter 1104 moveable for disposition over and in alignment with the signal receiver 118 of the implant housing 110. The transmitter 1106 and the implant housing 110 and/or signal receiver 118 may each include one or more magnets to facilitate retentive juxtaposed positioning. Thus, the external charging system can be operative to transcutaneously, for example, inductively couple with and the signal receiver 118 to provide power to the device. Further, RF communication between the devices is possible for data communication purposes. It should be understood that it is expected that the transmitter 1104 when used to transmit energy to the device for powering the device will need to placed very close to the device, whereas a transmitter 1104 used for data communication need not be so close.

Referring to FIGS. 3-4, it is noted that microphone assembly 130 in the present embodiment is a pendant microphone, which is connected to the implant housing 110 via a signal cable 124. Use of such a pendant microphone allows the microphone assembly 130 to be spaced from the implant housing 110. However, it will be appreciated that in other embodiments, the microphone may be mounted or integrally formed on or within the implant housing 110.

The microphone assembly 130 includes a diaphragm 132 that is positioned to receive ambient acoustic signals through overlying tissue, a microphone transducer (not shown) for generating an output signal indicative of the received ambient acoustic signals, and a housing 134 for supporting the diaphragm 132 relative to the transducer. As shown, the microphone assembly 130 is mounted in location spaced from the implant housing 110 and the cable 124 interconnecting the implant housing 110 and the microphone assembly 130 may be routed subcutaneously to the implant housing 110.

During normal operation, acoustic signals are received subcutaneously at the diaphragm 132 of the microphone assembly 130. The microphone assembly 130 generates an output signal that is indicative of the received acoustic signals. The output signal is provided to the implant housing 100 via the signal cable 124. Upon receipt of the output signal, a signal processor 112, within the implant housing 100, processes the signals to identify OSA precursors. As will be appreciated, the signal processor 112 may utilize digital processing techniques to provide frequency shaping, amplification, spectral analysis, and other signal conditioning, including conditioning based on patient-specific parameters.

The processor 112 is coupled to a memory by a suitable data/address bus, such that programmable operating parameters used by the processor can be stored and modified, as required, in order to customize the operation of the device 100 to suit the needs of a particular patient. Such operating parameters define, for example, (sleep) apnea detection criteria (rion), stimulation pulse amplitude(s) and frequency(ies), accelerometer signals, maintenance pulse amplitude, pulse duration, electrode polarity, etc. The memory may be used by the processor to load instructions and data of AHIPE Discrimination module 114 and Pulse Generation module 116 for execution by the processor. Such instructions and data may be initially stored in non-volatile memory (e.g., EEPROM, Flash, etc.) and loaded into internal memory of processor and/or memory. Further, as the processor is operatively interconnected to the signal receiver 118, additional data or operating instructions may be uploaded to the implant device 100.

In the present embodiment, a signal cable 138 extends between the implant housing 110 and the stimulation electrode 140. The cable 138 allows positioning of the electrode 140 within the soft tissue of the throat of the patient. As will be appreciated, the wire 138 may be routed using, for example, a flexible catheter, a trocar, cannula, etc.

In further arrangements, the implant housing 110 and/or the microphone housing 134 may further incorporate a motion sensor (see FIG. 10) that is adapted to generate a motion output signal. For instance, such a motion sensor may be implemented as an accelerometer that generates an output signal that is indicative of vibration or other movement received by implant housing and/or microphone housing. This motion sensor output signal may be utilized in conjunction with the microphone output signal to identify AHIPE events, as is further discussed herein.

Figure 6:
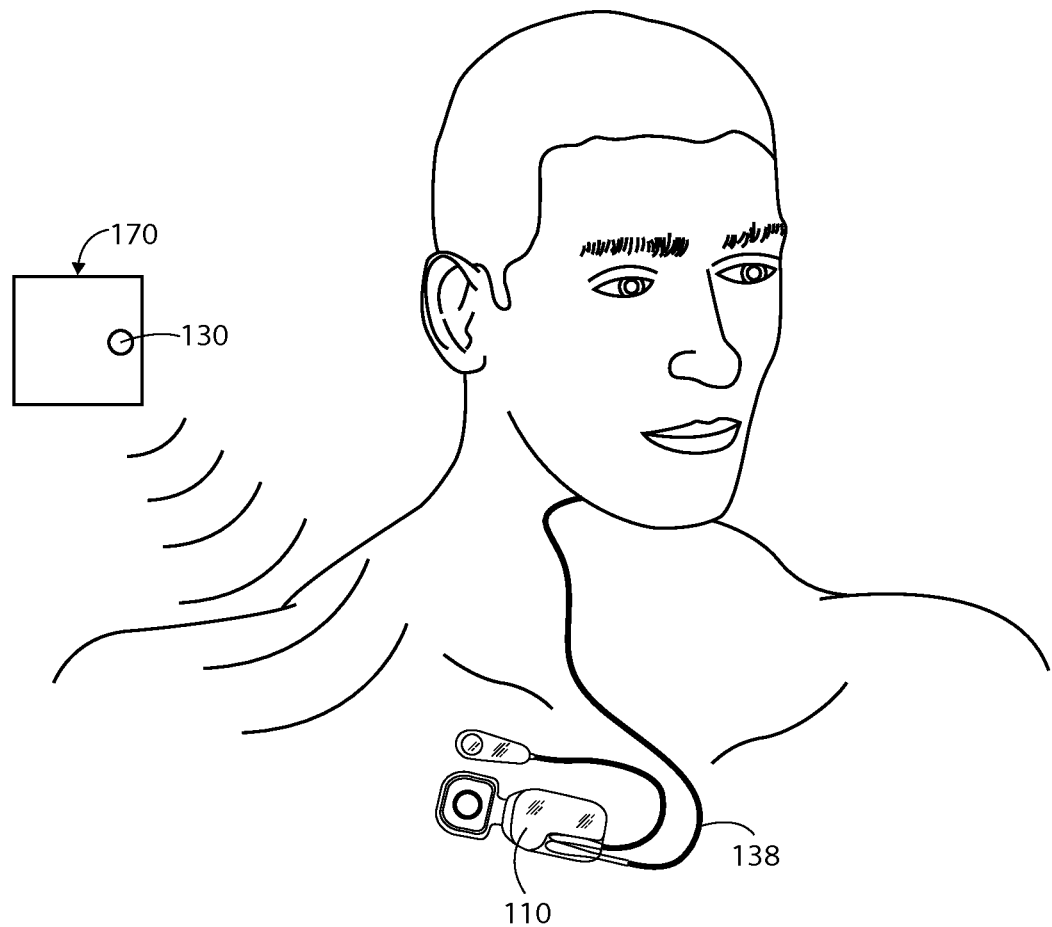
FIG. 6 illustrates an exemplary embodiment of a semi-implantable OSA treatment device.

FIG. 6 illustrates an alternate embodiment of the device. In this embodiment, the device includes an external unit 170, which communicates wirelessly with the implant housing 110. In this embodiment, the microphone assembly 130 may be incorporated into the external unit 170 and the external unit may be placed proximate to the user during sleep. In such an arrangement, the external unit may communicate (e.g., via RF signals) a microphone output signal to the implant housing for processing. Alternatively, some or all of the processing capability may be performed in the external unit 170 and the signals sent to the implant housing may be actuation signals dictating when and how much stimulus the electrode provides. Placing the microphone and signal processing externally has the advantage of reducing the power consumption in the implant, as well as potentially facilitating more sophisticated signal processing. Further still, the external unit 170 can be combined with the external charging system such that the external unit 170 is also configured to provide the functionality described above in connection with the external charging system of FIG. 11.

Figure 7:
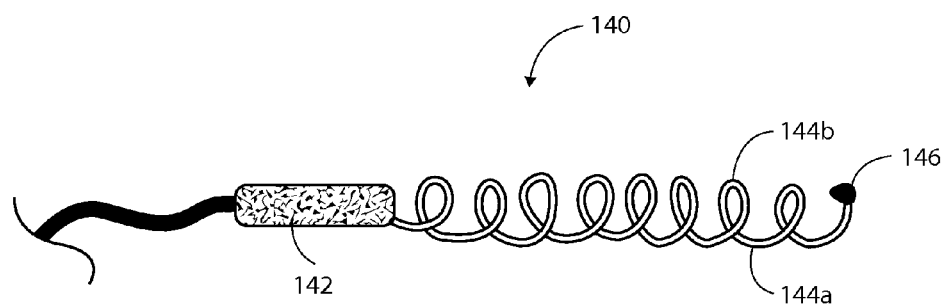
FIG. 7 illustrates an exemplary embodiment of a stimulation electrode.

FIG. 7 illustrates one embodiment of an electrode 140 that may be utilized with the OSA device. In the present embodiment, the electrode 140 includes first and second electrodes 142, 146 that are interconnected by first and second stands of coated (e.g., PTFE) signal wires 144a, 144b (hereafter 144). The use of first and second electrodes 142, 146 allows for providing electrical stimulus over a controlled volume to achieve improved tissue contraction. The signal wires 144 are coiled to permit improved flexibility for the electrode 140. That is, the wires while coated, are necessarily formed from bio-inert metals as the ends of these wires may be or may become partially exposed where they interconnect to the electrodes 142, 146. It has been determined that gold, while providing desired bio-inert and flexibility (e.g., ductility) properties, is generally too soft to form a durable electrode. Accordingly, more durable bio-inert materials are generally utilized to form the wires (e.g., a platinum-iridium alloy). While providing the necessary bio-inert qualities, these materials are relatively stiff in comparison to more commonly utilized wiring materials (e.g., gold, copper). Accordingly, to provide the flexibility necessary for an electrode that will be implanted at the base of the tongue, the wires 144a, 144b are coiled (e.g., helically). Such coiling allows the electrode to act as a spring and bend along its length. In one embodiment, the device utilizes bipolar electrodes to minimize interference with other biological and technological structures. Specifically, it is believed that bi-polar electrodes minimize actuation of peripheral musculature, as well as essentially eliminate interference with pacing, defibrillation, etc. implants and the like. However, it will be appreciated that the device is not limited to bipolar electrodes.

AHIPE Analysis

In any embodiment, the OSA device has to identify OSA precursors in order to prevent and/or alleviate OSA events. A good AHIPE candidate is the acoustic and/or vibration signatures of snoring. There is a strong correlation between snoring and OSA events, with a symptom of partial collapse of the upper airway typically initially resulting in snoring prior to a full apnea event. Some estimates indicate that various forms of OSA can be diagnosed with a sensitivity of 70% and specificity of 80% from audio recordings alone. Accordingly, it is evident that merely using the amplitude of sound, without any effort to discriminate other snoring features from background noise often yields a good estimate of when hypoxia will occur. Further examination of snoring records show that snoring occurs before actual apnea, and before and during hypopnea.

Figure 8:
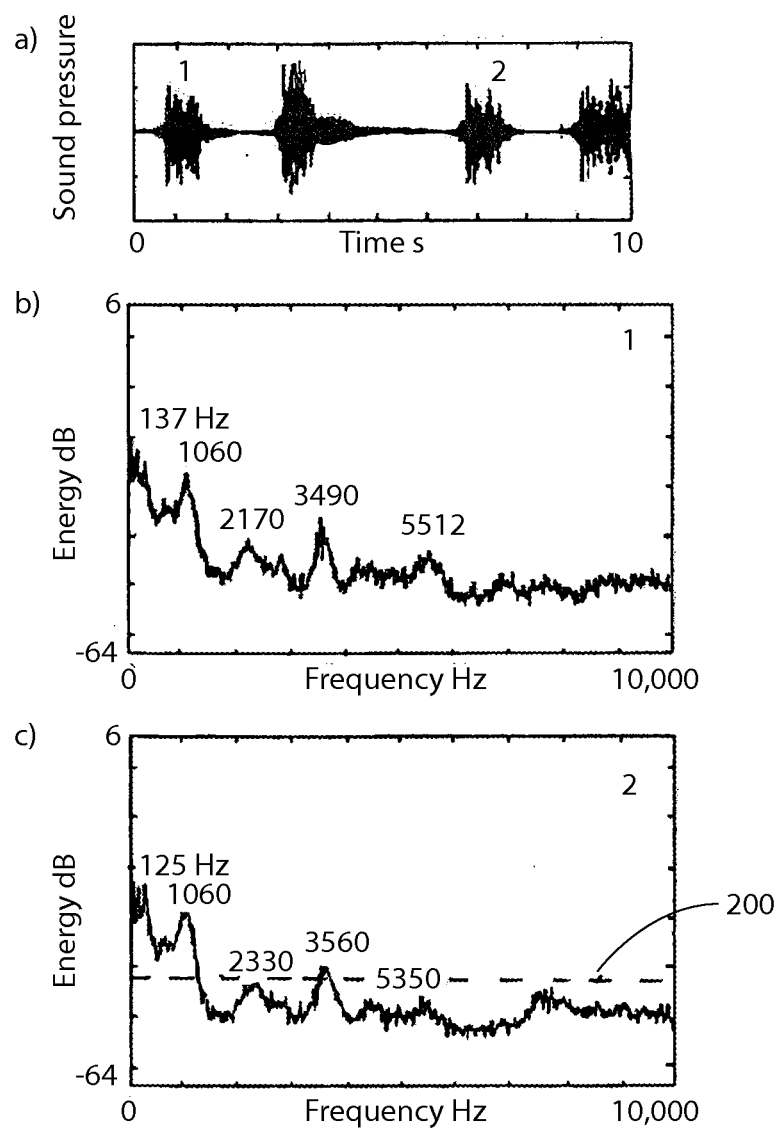
FIGS. 8a-8c illustrate temporal and spectral characteristics of snoring.
Figure 9A:
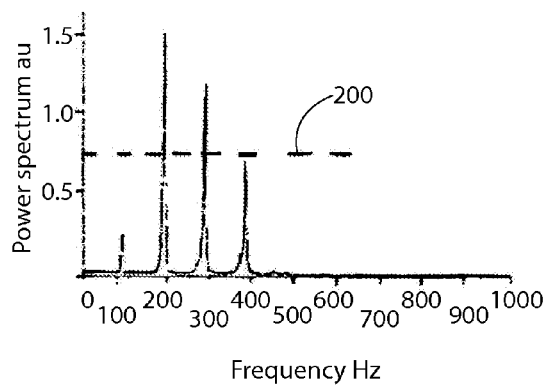
FIGS. 9a-9b illustrate spectral densities of simple snoring and OSA snoring.
Figure 9B:
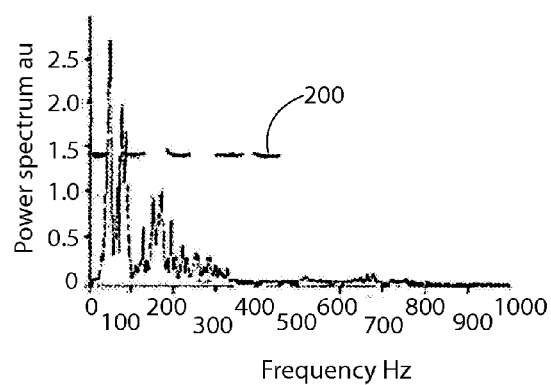

FIGS. 8 and 9 illustrate temporal and spectral properties and the power spectrum of snoring, respectively. As illustrated in FIG. 8a, snoring is often identified by regular intervals. Accordingly, in various aspects, simple filtering identifies when monitored sound is no longer regular. Alternatively, a magnitude or amplitude threshold 200 may be established. See FIGS. 8c and 9. It will be appreciated that, upon the sound level or power of a monitored signal exceeding such a threshold 200, the OSA device 100 may deliver stimulation via the electrode. Such thresholds may be varied by frequency and/or may be specific to a particular patient.

Studies have been performed which show that not only is snoring in general strongly correlated with OSA, but that simple (non-OSA) snoring may be distinguished from OSA snoring with good sensitivity and low false positive rates. The OSA device in its simplest form does not perform this more difficult task of discriminating between simple and OSA snoring, but detects snoring of either type and responds to both. However, it will be appreciated that other embodiments may distinguish between snoring and OSA snoring and only provide stimulation in response to OSA snoring. AHIPE discrimination is further discussed below.

It should be understood that an AHIPE other than snoring can be detected by the processor. For example, there are distinctive sounds during breathing, even though such sounds are not classifiable as snoring. For instance, a vigorous inhalation has a higher mean frequency (pitch) than an equally vigorous exhalation. The rushing sound is generated by the turbulence of the air flowing through the airway, and not by tissues impacting on each other. The inhalation has a higher frequency than the exhalation because the airway is pulled to a smaller shape by the negative pressure of the inhalation, whereas the airway is pushed to a larger shape by the positive pressure of the exhalation. The frequency of the turbulence is determined in part by the volume of airflow, and in part by the geometry (including size) of the airflow. Thus, a sensor that is sufficiently sensitive to detect quiet breathing can be deployed, and the processor can be configured to analyze the sensor data (e.g., via frequency analysis) to determine whether a breathing condition exists that is indicative of an apnea-related event.

Further still, it should be understood that these snoring, breathing or other AHIPE characteristics can detectably manifest themselves not only in sound data but also in motion data such as the vibratory signature of a person.

Another aspect of the OSA device is that, in a primary embodiment, the OSA device opens the upper airway by stimulus of the posterior genioglossus muscle. See FIG. 5. The genioglossus is a muscle of the human body which runs from the chin to the tongue. The genioglossus is the major muscle responsible for protruding (or sticking out) the tongue. Aspects of the present invention are based on the realization that the UA may be opened by direct stimulus to the genioglossus, particularly the posterior genioglossus. This is in contrast to previous systems that provide the neurostimulation of the hypoglossal nerve.

Further, the presented device provides stimulation prior to an apnea event as it has been demonstrated that the genioglossus in hypoxia responds less vigorously than a normally oxygenated genioglossus. This means a system that prevents OSA should be more successful than a rescue system that helps the patient recover from OSA. Additionally, it is easier to maintain an open UA than it is to open an obstructed UA.

In use the patient activates the device 100 before going to sleep using a wireless remote control which may be held over the coil 118 on the implant housing 110. Since it is typically more difficult to fall asleep from being wide awake than it is to fall back asleep from arousal, and since loss of tonus occurs only in the deepest levels of sleep, no stimulation is provided immediately after activation for a period of time, which for most patients is about 45 minutes. However, this delay interval may be set on a patient-by-patient basis. In any case, the delay interval allows a patient to fall asleep initially without experiencing any potentially disturbing sensations. After this initial mode, the implant goes into normal operation. This normal operation can be thought of as being in either the sustained or AHIPE modes.

Sustained mode is a low level stimulus that is activated periodically when the implant is not in initial or AHIPE mode. This typically is programmed to provide a mild, constant tonus stimulus that supplements the patient's sleeping tonus, and prevents the genioglossus from becoming completely atonic for a sustained period of time. One reason for this mode is that it has been found that it requires more stimulus to open the UA than it does to sustain the UA at a given level of opening. However, the sustained mode need not be continuous but may, rather, include the provision of periodic stimulation tones or pulses. Before AHIPE is detected, the implant continues to stimulate in the sustained mode.

When the implant detects AHIPE, the AHIPE mode is initiated and the OSA device provides a stronger AHIPE stimulus level. In this regard, a higher amplitude or duration stimulation signal is delivered to the electrode to activate the posterior genioglossus. As a sufficient electrical stimulus will typically prevent AHIPE, it may be difficult to detect AHIPE while stimulating in AHIPE mode. The implant therefore continues to stimulate in AHIPE for a predetermined period (e.g., a minute, or other user specific setting) after snoring has actually been detected. At the end of that period, AHIPE stimulation is stopped, and sustaining stimulus resumed until AHIPE is again detected.

In various arrangements, the stimulus levels applied by the electrode may servo within an allowed range of parameters to minimize AHI. That is, the relatively simple control described above is sufficient to allow the AHI number to be significantly reduced, although it is not guaranteed to reduce AHI to zero. It must be borne in mind that AHI<10 events per hour is considered normal, and reduction of AHI to zero is not a realistic goal. Reduction of AHI 50% of the way to normal levels of 10, and/or to a level of 5, 10 or 20 events per hour, should be considered as successful, as these levels greatly improve the patients quality of life.

Microphone/Accelerometer and Preprocessing

The process of detecting snoring events is performed primarily using acoustic monitoring. Generally, the devices utilize a microphone to monitor ambient acoustic sounds. The microphone may be implanted (See FIGS. 3 and 4) or part of an external unit (See FIG. 6). Further a motion sensor (e.g., accelerometer) monitors body borne vibrations. A signal indicative of an ambient snoring sound should correlate well with a vibration signal of a motion sensor (e.g., an accelerometer). That is, snoring should induce a vibration within the body. Through the use of cancellation techniques, it is possible to separate externally generated acoustic signals (e.g., snoring and environmental sounds) based on internally generated vibration. This method is similar to a directional microphone that looks inward to the body, which allows signals arising from environmental sources external from the body to be greatly reduced in the microphone output signal. This allows for more readily isolating a snoring signature from a microphone output signal, which will also include environmental noises (e.g., television, door slamming etc.). Such isolation may reduce the false identification of OSA precursor events. Another approach is combining the acoustic and vibration signals in a manner to optimally discriminate AHIPE from both acoustic and vibrational noise. Noise in this context may be any signal that is not AHIPE.

Figure 10:
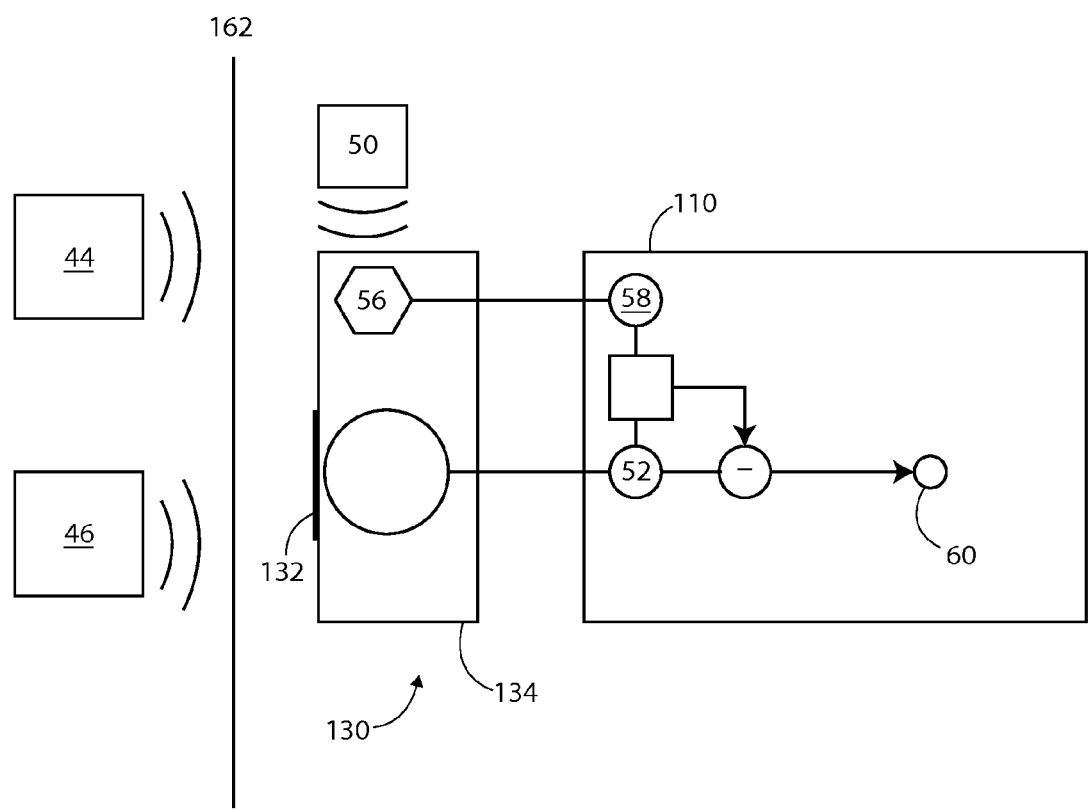
FIG. 10 illustrates an implantable microphone incorporating a motion sensor.

The block diagram of FIG. 10, illustrates cancellation of environmental noises from a microphone output signal of an implanted microphone. The microphone output signal includes responses resulting from both ambient acoustic sounds and tissue-borne vibration caused by body vibrations/movement (e.g., snoring). Generally, the ambient sounds and tissue-borne vibration are combined at the implanted microphone diaphragm 132. As shown, the implanted microphone diaphragm 132 is exposed to pressure in overlying tissue 162 that is generated externally to the patient by both desired ambient sound sources 44 (e.g., patient snoring) and undesired ambient sound sources 46 (environmental noise). The ambient signals (e.g., sound) from the sound sources pass through the tissue 162 overlying the microphone diaphragm 132. The deflection of the microphone diaphragm 132 by the pressure associated with the ambient sound results in a microphone sound response 52. This microphone sound response 52 includes desired ambient sounds 44 (e.g., snoring) and undesired ambient sounds (environmental noise) 46. In order to isolate the desired ambient signal component (e.g., the microphone snoring response) with sufficient sensitivity, the implanted microphone needs to compensate for undesired ambient signal components (e.g., ambient environmental noise). In order to separate these signals, one element of the microphone assembly 132 is designed to be preferentially sensitive to tissue borne vibration and preferentially insensitive to ambient acoustic stimulation.

Specifically, the microphone housing or implant housing includes a motion sensor 56 that is primarily sensitive to tissue-borne vibration (i.e., acceleration) while being substantially insensitive to ambient acoustic signals. In this regard, an output 58 from the motion sensor 56 may be correlated with the output 52 from an implanted microphone diaphragm 132. Accordingly, by correlating the responses of the microphone with the response of the motion sensor, information in the microphone output signal that does not correspond to the output signal 58 of the motion sensor may be considered environmental noise and eliminated from the microphone output signal. Stated otherwise, the snoring signature in the microphone signal 52 should correspond to the snoring signature in the motion sensor output signal 58. Irrelevant information in the microphone output signal 52 may be removed to provide a signal 60 that preferentially represents the snoring of a patient. In essence, the motion sensor output signal becomes a filter for the microphone output signal.

AHIPE Discrimination

As noted, detecting the change in acoustic and vibration amplitudes is useful in predicting AHI events. However, better OSA prediction can be achieved with more sophisticated signal processing. For instance, detecting snoring and distinguishing it from various background noises is relatively easy with the appropriate sensors and signal processing capability. Snoring, for instance, has fairly well-defined temporal and spectral properties (FIG. 8a). Snoring also has the same period as breathing, and as seen in FIG. 8a. Further, the energy in a monitored signal is concentrated in the frequency range<1 kHz as seen in FIGS. 8b and 8c. Another example is shown in FIG. 9, which illustrates the difference between simple snoring and OSA snoring spectral densities. The AHIPE discriminator has a number of feature detectors, based on the temporal, spectral, and other characteristics of the sensor signals. Each of these feature detectors estimate a particular parameter extracted from the sensor signals. Some of these parameters are analog, and include the signal power in each of several bandwidths and/or the minimum and peak signal amplitude. Some of these parameters are Boolean, and include windowing the duration and period of the signal that are "snoring-like" within allowed intervals. These signals are then combined by a decision-making algorithm which is designed to optimize discriminating AHIPE from non-AHIPE, while appropriately limiting misclassification. The consequences of false positives (detecting AHIPE when no apnea, in fact, exists) are milder than false negatives (not detecting AHIPE when apnea exists). Such false positives may be induced by simple snores and other noises with similar temporal, spectral, etc., properties of OSA snores.

One suspected consequence of detecting a false positive OSA snore may be muscle fatigue if the genioglossus is stimulated continuously and vigorously all night. However, detecting false positive AHIPE for a small fraction of the sleep period is acceptable, as is mild stimulation. A consequence of detecting a false positive may be activating the genioglossus during a simple snore, rather than an AHIPE. This has the effect of reducing the number of simple snores during the night. This is beneficial not simply from the social impact of snoring, but because it has been demonstrated that OSA is, in part, due to desensitization of the normal genioglossus reflex which prevent the upper airway (UA) from collapsing. This has been shown to occur from the desensitization of the topical sensory nerves of the UA, which could occur due to simple snoring. As a result, false positives due to detecting simple snoring, is not only an acceptable error, but may be considered beneficial.

One source of false positive detection is environmental noises. It is thus recommended that the patient practice good sleep hygiene and sleep in a relatively quiet area (typically<60 dBA, and preferably less), free from confounding signals such as television or radio programs. This is of benefit to the patient as well as optimal performance of the implant. However, it is beneficial to compare the ambient information received from the microphone (e.g., snoring sounds and environmental information) with the motion noise received from the accelerometer (e.g., snoring/breathing induced vibration substantially free of ambient sound) to filter environmental noise form the monitored signal. Further, it is desirable to allow the AHIPE features of the signal processor to discriminate against common environmental noises and/or other potentially confounding signals which may induce false positives. Such other sounds may include, for example, pulmonary sounds, coughing, rales, crackles, stridor (partial obstruction of the larynx), rhonchi (wheezes), etc. Again, such information may be generalized or patient specific. In most cases, the consequences of false positives (and subsequently opening up the oropharynx) is mild compared to false negatives. As a result of the mild consequences of false positives, and the deprivation of therapy for false negatives, the discrimination algorithm is weighted to make far fewer false negative than false positives. However, the sensitivity of the OSA device (e.g., false positives) may be set based on user specific needs.

Electrical Stimulus

Both the sustained and AHIPE stimulus levels are fully independently programmable. The stimulus levels are biphasic with balanced net electrode charge to minimize corrosion and morbidity. The pulses have a programmable amplitude of approximately 2-12V peak, and may also be set to 0 VDC or open circuit. This range was selected for the pulse parameters (see below), as 6V peak is approximately the minimum of sensation, while 12V is approximately the maximum a patient can tolerate. Each pulse is positive for a programmable 30-300 usec duration, then very briefly zero or open circuit, then negative for a corresponding 30-300 usec. These pulses are repeated at a programmable repetition rate of 25-300 Hz. This pulse train may be further modulated by an overall envelope allowing the device to be activated on and off with any predetermined stimulation pattern. It will be appreciated that other stimulation levels are possible and considered within the scope of the presented device.

The foregoing description has been presented for purposes of illustration and description. Furthermore, the description is not intended to limit the inventions and/or aspects of the inventions to the forms disclosed herein. Consequently, variations and modifications commensurate with the above teachings, and skill and knowledge of the relevant art, are within the scope of the presented inventions. The embodiments described hereinabove are further intended to explain best modes known of practicing the inventions and to enable others skilled in the art to utilize the inventions in such, or other embodiments and with various modifications required by the particular application(s) or use(s) of the presented inventions. It is intended that the appended claims be construed to include alternative embodiments to the extent permitted by the prior art.

What is claimed is:

1. A stimulation system comprising:
   a sensor configured to generate sensor data, the sensor data including information indicative of whether a person is snoring, the sensor comprising at least one member of the group consisting of a microphone and a motion sensor;
   a processor configured to (1) process the sensor data, (2) based on the processed sensor data, distinguish between obstructive sleep apnea (OSA) snoring and non-OSA snoring, and (3) generate a stimulation signal in response to a determination that OSA snoring is indicated by the processed sensor data; and
   a stimulation electrode adapted for positioning to provide an electrical stimulation to a sleep apnea treatment location for a person, wherein the stimulation electrode is configured to (1) receive the generated stimulation signal from the processor, and (2) generate an electrical stimulation output in response to the received stimulation signal.

2. The system of claim 1 wherein the sensor comprises a microphone, the microphone configured to generate a microphone output signal, the microphone output signal being indicative of an ambient acoustic signal, and wherein the sensor data comprises the microphone output signal.

3. The system of claim 2 wherein the stimulation electrode is adapted for positioning to provide an electrical stimulation to at least one of a genioglossus muscle and a hypoglossal nerve.

4. The system of claim 3 wherein the microphone comprises a diaphragm operative to move in response to forces present in media overlying the diaphragm.

5. The system of claim 4 wherein the microphone comprises an implantable microphone.

6. The system of claim 3 further comprising an implantable housing, the processor being disposed within the implantable housing.

7. The system of claim 6 wherein the microphone is disposed within the implantable housing.

8. The system of claim 2 wherein the processor is further configured to distinguish between OSA snoring and non-OSA snoring via apnea and hypopnea index precursors and events (AHIPE) discrimination based on a plurality of features of the sensor data.

9. The system of claim 8 wherein the processor is further configured with a plurality of feature detectors, the feature detectors configured to estimate a plurality of parameters from the sensor data based on temporal and spectral characteristics of the sensor data, and wherein the processor is further configured to perform the AHIPE discrimination to distinguish between OSA snoring or non-OSA snoring based on the estimated parameters.

10. The system of claim 9 wherein the estimated parameters comprise at least one member of the group consisting of (1) signal power in each of a plurality of bandwidths for the sensor data, (2) minimum and peak signal amplitude for the sensor data.

11. The system of claim 2 wherein the microphone comprises an implantable microphone, the implantable microphone comprising a diaphragm operative to move in response to forces present in media overlying the diaphragm, the sensor further comprising a motion sensor configured to generate a motion signal indicative of motion of at least one of the implant housing and the implantable microphone, the system further comprising:
   an implantable housing, the processor being disposed within the implantable housing.

12. The system of claim 11, wherein the motion sensor comprises an accelerometer.

13. The system of claim 11, wherein the processor is further configured to (1) receive the motion signal, (2) correlate the microphone output signal with the motion signal to isolate a snoring signature within the sensor data from environmental noise, and (3) process the isolated snoring signature to determine whether the isolated snoring signature is indicative of OSA snoring.

14. The system of claim 13 wherein the processor is further configured to process the motion signal to identify a vibratory signature of the motion signal that corresponds to a predetermined OSA precursor snoring signature.

15. The system of claim 2 wherein the microphone comprises an implantable microphone, the implantable microphone comprising a diaphragm operative to move in response to forces present in media overlying the diaphragm, the system further comprising:
   an implantable housing, the processor being disposed within the implantable housing; and
   an implantable power storage device for powering the microphone, the processor and the stimulation electrode.

16. The system of claim 15 wherein the implantable power storage device is disposed within the implantable housing.

17. The system of claim 2 further comprising:
   an implantable housing, the processor being disposed within the implantable housing; and
   a wireless transceiver operatively connected to the implant housing, the transceiver configured to transcutaneously transmit and receive at least one of power and data.

18. The system of claim 2 wherein the processor is further configured to generate first and second stimulation signals, wherein an intensity of the first and second stimulation signals is different, and wherein the stimulation electrode is further configured to generate first and second different electrical stimulation outputs in response to the first and second stimulation signals.

19. The system of claim 18 wherein the processor is further configured to (1) generate the first stimulation signal in response to a determination that OSA snoring is indicated by the processed sensor data, and (2) generate the second stimulation signal on a predetermined schedule.

20. The system of claim 19 wherein the predetermined schedule is a periodic schedule.

21. The system of claim 2 wherein the processor is further configured to (1) extract a plurality of features from the microphone output signal that are indicative of a power spectrum characteristic for a snoring signature indicated by the sensor data and (2) determine whether the snoring signature corresponds to OSA snoring based on the extracted features.

22. The system of claim 2 wherein the stimulation electrode comprises:
a first electrode adapted to stimulate a first location of a physiological structure; and
a second electrode adapted to stimulate a second location of the physiological structure.

23. The system of claim 2 wherein the stimulation electrode comprises:
a first electrode adapted to stimulate a first physiological structure; and
a second electrode adapted to stimulate a second physiological structure.

24. The system of claim 2 wherein the stimulation electrode comprises a bi-polar electrode.

25. The system of claim 24 wherein the electrical stimulation output of the stimulation electrode has an amplitude of between about 4.1 Volts peak and about 12 Volts peak.

26. The system of claim 24 wherein stimulation electrode is further configured to generate the electrical stimulation output as a plurality of pulses.

27. The system of claim 26 wherein the pulses have a duration of between 30-300 μsec and a repetition rate of 25-300 Hz.

28. The system of claim 24 wherein the stimulation electrode comprises a flexible stimulation electrode.

29. The system of claim 2 wherein the stimulation electrode is adapted for positioning to contact an interior portion of a genioglossus muscle.

30. The system of claim 2 wherein the stimulation electrode is adapted for positioning proximate to a genioglossus muscle.

31. The system of claim 30 wherein the stimulation electrode is adapted for positioning to contact the genioglossus muscle to directly stimulate the genioglossus muscle with the electrical stimulation output.

32. The system of claim 31 wherein the stimulation electrode is further adapted positioning to contact the posterior genioglossus muscle to directly stimulate the posterior genioglossus muscle with the electrical stimulation output.

33. The system of claim 2 wherein the processor comprises an external processor.

34. The system of claim 2 wherein the microphone comprises an external microphone device.

35. The system of claim 34 further comprising:
a wireless transmitter configured to transmit the microphone output signal;
an implantable housing, the processor being disposed within the implantable housing, the implantable housing further comprising a wireless receiver, the wireless receiver configured to receive the microphone output signal.

36. The system of claim 35 further comprising:
a rechargeable power storage device, the rechargeable power storage device configured to power at least the wireless receiver, the processor and the stimulation electrode.

37. The system of claim 34 wherein the processor is resident in the external microphone device, the system further comprising:
a wireless transmitter configured to transmit the stimulation signal;
an implantable wireless receiver, the wireless receiver configured to receive the stimulation signal and provide the stimulation signal to the stimulation electrode.

38. The system of claim 1 wherein the sensor comprises a motion sensor.

39. The system of claim 1 wherein the processor is further configured with a programmable delay interval to define a time period during which a stimulation signal will not be generated.

40. The system of claim 1 further comprising a memory, the memory configured to store a plurality of operating parameters for use by the processor to provide customized operation for a person.

41. The system of claim 1, wherein the processor is further configured to operate in a plurality of modes, the modes including a first mode and a second mode;
wherein the processor, when in the first mode, is configured to generate a first stimulation signal for delivery to the stimulation electrode;
wherein the processor, when in the second mode, is configured to generate a second stimulation signal for delivery to the stimulation electrode, the second stimulation signal comprising a periodic stimulation signal that accords with a predetermined schedule; and
wherein the processor is configured to switch between the first mode and the second mode based on whether there is a determination that OSA snoring is indicated by the processed sensor data such that the processor is configured to operate in the first mode in response to a determination that OSA snoring is indicated by the processed sensor data.

42. The system of claim 41 wherein the processor is further configured to (1) extract a plurality of features from the sensor data that are indicative of a power spectrum characteristic for a snoring signature indicated by the sensor data, and (2) determine whether the snoring signature corresponds to OSA snoring based on the extracted features.

43. The system of claim 42, wherein the stimulation electrode is further configured to (1) provide a first electrical stimulation to the sleep apnea treatment location in response to the first mode stimulation signal, and (2) provide a second electrical stimulation to the sleep apnea treatment location in response to the second mode stimulation signal, the first electrical stimulation being stronger than the second electrical stimulation.

44. The system of claim 43 wherein the processor is further configured to operate in a third mode, wherein the processor, when in the third mode, is configured to not generate any stimulation signal.

45. The system of claim 44 wherein the processor is further configured to (1) operate in the third mode for an initial delay interval, and (2) after the initial delay interval, switch between the first and second operating modes based on whether a determination is made that OSA snoring is indicated by the processed sensor data.

46. The system of claim 42 wherein the processor is further configured to generate the stimulation signals for the first and second modes in accordance with a plurality of programmable parameters that control a plurality of characteristics for electrically stimulating the sleep apnea treatment location.

47. The system of claim 1, wherein the processor is further configured to (1) operate in a first mode for an initial delay interval, (2) after the initial delay interval and in response to a determination that OSA snoring is indicated by the sensor data, operate in a second mode for a predetermined time period, and (3) after the initial delay interval and in response to a determination that OSA snoring is not present based on the sensor data, operate in a third mode;

wherein the processor, when in the third mode, is configured to generate a stimulation signal for indicating that the sleep apnea treatment location for the person is to be electrically stimulated in accordance with a predetermined schedule;

wherein the processor, when in the second mode, is configured to generate a stimulation signal for indicating that a sleep apnea treatment location for the person is to be electrically stimulated; and wherein the processor, when in the first mode, is configured to not generate a stimulation signal.

48. The system of claim 47, wherein the stimulation electrode is further configured to (1) provide a first electrical stimulation to the sleep apnea treatment location in response to the second mode stimulation signal, and (2) provide a second electrical stimulation to the sleep apnea treatment location in response to the third mode stimulation signal, the first electrical stimulation being stronger than the second electrical stimulation.

49. The system of claim 48, further comprising:
   a wire that connects the processor and the stimulation electrode, wherein the wire comprises a member of the group consisting of: a flexible catheter, a trocar, and a cannula.

50. The system of claim 6, wherein the implantable housing is adapted to be located below the person's clavicle.

51. The system of claim 2 further comprising:
   an implantable housing, the processor being disposed within the implantable housing; and
   an energy storage device for powering the processor and the stimulation electrode, wherein the energy storage device is disposed within the implantable housing; and
   wherein the energy storage device is configured for transcutaneous re-charging from an external charging device.

52. The system of claim 51 wherein the energy storage device is configured for transcutaneous re-charging from the external charging device via inductive coupling with the external charging device.

53. The system of claim 51 wherein the implantable housing further comprises:
   a magnet positioned to facilitate retentive juxtaposed positioning with respect to a magnet of the external charging device.

54. The system of claim 53 further comprising:
   the external charging device, wherein the external charging device comprises a transmitter for transcutaneously transmitting a charge to the energy storage device, wherein the transmitter includes the magnet for facilitating retentive juxtaposed positioning with respect to the magnet of the implantable housing.

55. The system of claim 54 wherein the transmitter comprises a charger coil.

* * * * *